US011046757B2

(12) United States Patent
Borras et al.

(10) Patent No.: US 11,046,757 B2
(45) **Date of Patent: *Jun. 29, 2021**

(54) SOLUBILITY OPTIMIZATION OF IMMUNOBINDERS

(71) Applicant: Novartis AG, Basel (CH)

(72) Inventors: Leonardo Borras, Schlieren (CH); David Urech, Hombrechtikon (CH)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/267,460

(22) Filed: Feb. 5, 2019

(65) Prior Publication Data

US 2019/0169284 A1 Jun. 6, 2019

Related U.S. Application Data

(62) Division of application No. 15/378,649, filed on Dec. 14, 2016, now Pat. No. 10,221,237, which is a division of application No. 13/000,460, filed as application No. PCT/CH2009/000221 on Jun. 25, 2009, now Pat. No. 9,556,265.

(60) Provisional application No. 61/075,692, filed on Jun. 25, 2008.

(51) Int. Cl.
*C07K 16/22* (2006.01)
*C07K 16/24* (2006.01)

(52) U.S. Cl.
CPC ............ *C07K 16/241* (2013.01); *C07K 16/22* (2013.01); *C07K 2317/567* (2013.01); *C07K 2317/622* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,714,350 A | 2/1998 | Co et al. | |
| 5,736,137 A | 4/1998 | Anderson et al. | |
| 5,824,307 A | 10/1998 | Johnson | |
| 6,258,562 B1 | 7/2001 | Salfeld et al. | |
| 6,350,861 B1 | 2/2002 | Co et al. | |
| 6,455,043 B1 | 9/2002 | Grillo-Lopez | |
| 6,602,977 B1 | 8/2003 | Ljungqvist | |
| 6,673,901 B2 | 1/2004 | Koide | |
| 6,682,734 B1 | 1/2004 | Anderson et al. | |
| 6,703,199 B1 | 3/2004 | Koide | |
| 6,740,734 B1 | 5/2004 | Nilsson et al. | |
| 6,815,540 B1 | 11/2004 | Pluckthun et al. | |
| 6,884,879 B1 | 4/2005 | Baca et al. | |
| 7,078,490 B2 | 7/2006 | Koide | |
| 7,119,171 B2 | 10/2006 | Koide | |
| 2007/0031413 A1 | 2/2007 | Fyfe et al. | 424/145.1 |

FOREIGN PATENT DOCUMENTS

| | | | |
|---|---|---|---|
| EP | 0938506 | B1 | 11/2003 |
| EP | 1242457 | B1 | 8/2004 |
| EP | 1479694 | A2 | 11/2004 |
| JP | 2000-516452 | | 12/2000 |
| WO | 199916873 | | 4/1999 |
| WO | 200063243 | | 10/2000 |
| WO | 200148017 | A1 | 7/2001 |
| WO | 0162931 | A2 | 8/2001 |
| WO | 200164942 | A1 | 9/2001 |
| WO | 200220565 | A2 | 3/2002 |
| WO | 2002088171 | A2 | 11/2002 |
| WO | 2003097697 | A2 | 11/2003 |
| WO | 2004044011 | A2 | 5/2004 |
| WO | 2005019254 | A1 | 3/2005 |
| WO | 2006083275 | A2 | 8/2006 |
| WO | 2006131013 | A2 | 12/2006 |
| WO | 2008006235 | A2 | 1/2008 |
| WO | 2008110348 | A1 | 9/2008 |
| WO | 2009000098 | A2 | 12/2008 |
| WO | 2009000099 | A2 | 12/2008 |
| WO | 2009155725 | A1 | 12/2009 |

OTHER PUBLICATIONS

Ewert, Stefan et al., "Stability Improvement of antibodies for extracellular and intracellular applications: CDR grafting to stable frameworks and structure-based framework engineering" Methods, vol. 34, pp. 184-199, 2004.
Ohba, H et al.: Host: EMBL, No. BAB33407.1 Apr. 14, 2007.
Souza, T et al. Host: EMBL, No. ABK81278.1 Aug. 29, 2007.
Losman, M et al. Host: Kabat, No. 002674 Nov. 24, 1998.
Notice of Opposition against European Patent No. 2 307 455 (09 768 694.3) , "Solubility Optimization of Immunobinders", Patentee:ESBATech, an Alcon Biomedical Research Unit LLC., Opposition by Greaves Brewster LLP, p. 1-14, Dec. 21, 2017.
Urech, David, Prosecution History, Utility U.S. Appl. No. 14/308,936, filed Jun. 19, 2014, 3,342 pages.
Trevino; Amino Acid Contribution to Protein Solubility: Asp, Glu, and Ser Contribute more Favorably than the other Hydrophilic Amino Acids in RNase Sa; J. Mol. Biol.; ScienceDirect; 2007; pp. 449-460.
Davies and Riechmann, FEBS Letters 339 (1994) 285-290).
Neiba et al. (Protein Engineering, vol. 10, No. 4, pp. 435-444, 1997).
Protein Engineering, vol. 10, No. 4, pp. 435-444, 1997.
Arakawa et al.; "Cloning and sequencing of the VH and Vx genes of an anti-CD3 monoclonal antibody, and construction of a mouse/human chimeric antibody"; J. Biochem.; vol. 120; pp. 657-662 (1996).

(Continued)

*Primary Examiner* — Meera Natarajan
(74) *Attorney, Agent, or Firm* — Mythili Markokwski

(57) ABSTRACT

The invention provides methods of using sequence based analysis and rational strategies to improve the solubility of immunobinders, and in particular of single chain antibodies (scFvs). The invention provides methods of engineering immunobinders, and in particular scFvs, by performing one or more substitutions with hydrophilic residues identified by analysis of a database of selected, stable scFv sequences. The invention also provides immunobinders with optimized solubility prepared according to the engineering methods of the invention.

4 Claims, 7 Drawing Sheets

(56) References Cited

OTHER PUBLICATIONS

Atha and Ingham; "Mechanism of precipitation of proteins by polyethylene glycols"; The Journal of Biological Chemistry; vol. 256; No. 23; pp. 12108-12117 (Dec. 10, 1981).
Berge et al.; "Pharmaceutical salts" Review Article; Journal of Pharmaceutical Sciences; vol. 66; No. 1; pp. 2-19 (Jan. 1977).
Bird et al; "Single-chain antigen-binding proteins"; Science; vol. 242; pp. 423-426; (Oct. 21, 1988).
Cornette et al.; "Hydrophobicity scales and computational techniques for detecting amphipathic structures in proteins"; J. Mol. Biol.; vol. 195; pp. 659-685 (1987).
Davis et al.; "Camelising human antibody fragments: NMR studies on VH domains"; FEBS Letters; vol. 339; No. 3; pp. 285-290 (Feb. 21, 1994).
Davis et al.; "Single antibody domains as small recognition units: design and in vitro antigen selection of camelized, human VH domains with improved protein stability"; Protein Engineering; vol. 9; No. 6; pp. 531-537 (Jan. 1, 1996).
Dumoulin et al; "Single-domain antibody fragments with high conformational stability"; Protein Science; vol. 11; pp. 500-515 (2002).
Fisher et al.; "Efficient isolation of soluble intracellular single-chain antibodies using the Twin-arginine Translocation Machinery"; Journal of Molecular Biology; vol. 385; No. 1; pp. 299-311 (Jan. 9, 2009).
Hamers-Casterman et al; "Naturally occurring antibodies devoid of light chains"; Letters to Nature; vol. 363; pp. 446-448 (Jun. 3, 1993).
Honegger and Pluckthun; "Yet another numbering scheme for immunoglobulin variable domains: an automatic modeling and analysis tool"; J. Mol. Biol.; vol. 309; pp. 657-670 (2001).
Huston et al; "Protein engineering of antibody binding sites: recovery of specific activity in an anti-digoxin single-chain Fv analogue produced in *Escherichia coli*"; Proc. natl. Acad. Sci.; vol. 85; pp. 5879-5883 (Aug. 1988).
Jung and Pluckthun; "Improving in vivo folding stability of a single-chain Fv antibody fragment by loop grafting"; Protein Engineering; vol. 10; No. 8; pp. 959-966 (1997).
Jung et al.; "Selection for improved protein stability by phage display"; Journal of Molecular Biology; vol. 294; No. 1; pp. 163-180 ()Nov. 19, 1999).
Kung and Goldstein; "Monoclonal antibodies defining distinctive human T cell surface antigens"; Science; vol. 206; pp. 347-349 (Oct. 19, 1979).
Needleman and Wunsch; "A general method applicable to the search for similarities in the amino acid sequence of two proteins"; J. Mol. Biol.; vol. 48; pp. 443-453 (1970).
Nieba et al.; "Disrupting the hydrophobic patches at the antibody variable/constant domain interface: improved in vivo folding and physical characterization of an engineered scFv fragment"; Protein Engineering; vol. 10; No. 4; pp. 435-444 (Jan. 1, 1997).
Rose et al.; "Hydrophobicity of amino acid residues in globular proteins"; Science; vol. 229; pp. 834-838 (Aug. 30, 1985).
Skerra and Pluckthun; "Assembly of a functioanl immunoglobulin Fv fragment in *Escherichia coli*"; Science; vol. 240; pp. 1038-1041 (May 20, 1988).
Tan et al.; "Contributions of a highly conserved VH/NL hydrogen bonding interaction to scFv folding stability and refolding efficiency"; Biophysical Journal; vol. 75; pp. 1473-1482 (Sep. 1998).
Ward et al; "Binding activities of a repertoire of single immunoglobulin variable domains secreted form *Escherichia coli*"; Letters to Nature; vol. 341; pp. 544-546 (Oct. 12, 1989).
Worn and Pluckthun; "Mutual stabilization of VL and VH in single-chain antibody fragments, investigated with mutants engineered for stability"; Biochemistry; vol. 37; pp. 13120-13127 (1998).
Worn and Pluckthun; "Different equilibrium stability behavior of ScFv fragments: identification, classification, and improvement by protein engineering"; Biochemistry; vol. 38; pp. 8739-8750 (1999).
Worn and Pluckthun; "Stability engineering of antibody single-chain Fv fragments"; J. Mol. Biol.; vol. 305; pp. 989-1010 (2001).
Knappik et al.; "Fully synthetic human combinatorial antibody libraries (HuCAL) based on modular consensus frameworks and CDRs randomized with trinucleotides"; J. Mol. Biol.; vol. 296; pp. 57-86 (2000).
Kushner et al.; "High-dose cyclophosphamide inhibition of humoral immune respopnse to murine monoclonal antibody 3F8 neuroblastoma patients: broad implications for immunotherapy"; Pediatr Blood Cancer; vol. 48; pp. 430-434 (2007).
Leonard et al; "Abbreviated chemotherapy with fludarabine followed by tositumomab and iodine I 131 tositumomab for untreated follicular lymphoma"; Journal of Clinical Oncology; vol. 23; No. 24; pp. 5696-5704 (Aug. 20, 2005).
Molineux; "Pegylation: Engineering Improved Biopharmaceuticals for Oncology" Pharmacotherapy; vol. 23; vol. 8 part 2; pp. 3S-8S (2003).
Nagata and Pastan; "Removal of B cell epitopes as a practical approach for reducing the immunogenicity of foreign protein-based therapeutics"; Advanced Drug Delivery Reviews; vol. 61; pp. 977-985 (2009).
Onda et al; "An immunotoxin with greatly reduced immunogenicity by identification and removal of B cell epitopes"; PNAS; vol. 105; No. 2; pp. 11311-11316 (Aug. 12, 2008).
Wang et al., "Antibody Structure, Instability, and Formulation", J. Pharma. Sciences. 96(1): 1-26 , (2007).
Kerwin, "Polysorbates 20 and 80 Used in the Formulation of Protein Biotherapeutics: Structure and Degradation Pathways", J. Pharma. Sciences. 97(8) :2924-2935, (2008).
Ajay K. Banga, "Therapeutic Peptides and Proteins—Formulation, Processingand Delivery Systems", First Edition, 1995.

SOLUBILITY OPTIMIZATION OF IMMUNOBINDERS

RELATED APPLICATIONS

The present application is a divisional of U.S. application Ser. No. 15/378,649 filed Dec. 14, 2016 (now Allowed), which is a divisional of U.S. application Ser. No. 13/000,460, a 371 application filed Dec. 21, 2010 (now U.S. Pat. No. 9,556,265), which claims priority from PCT/CH2009/000221, filed Jun. 25, 2009, which claims priority of U.S. 61/075,692, filed Jun. 25, 2008.

BACKGROUND OF THE INVENTION

Antibodies have proven to be very effective and successful therapeutic agents in the treatment of cancer, autoimmune diseases and other disorders. While full-length antibodies typically have been used clinically, there are a number of advantages that use of an antibody fragment can provide, such as increased tissue penetration, absence of Fc-effector function combined with the ability to add other effector functions and the likelihood of less systemic side effects resulting from a shorter in vivo half life systemically. The pharmacokinetic properties of antibody fragments indicate that they may be particularly well suited for local therapeutic approaches. Furthermore, antibody fragments can be easier to produce than full-length antibodies in certain expression systems.

One type of antibody fragment is a single chain antibody (scFv), which is composed of a heavy chain variable domain ($V_H$) conjugated to a light chain variable domain ($V_L$) via a linker sequence. Thus, scFvs lack all antibody constant region domains and the amino acid residues of the former variable/constant domain interface (interfacial residues) become solvent exposed. An scFv can be prepared from a full-length antibody (e.g., IgG molecule) through established recombinant engineering techniques. The transformation of a full length antibody into an scFv, however, often results in poor stability and solubility of the protein, low production yields and a high tendency to aggregate, which raises the risk of immunogenicity.

Accordingly, attempts have been made to improve properties such as solubility of scFvs. For example, Nieba, L. et al. (Prot. Eng. (1997) 10:435-444) selected three amino acid residues known to be interfacial residues and mutated them. They observed increased periplasmic expression of the mutated scFv in bacteria, as well as a decreased rate of thermally induced aggregation, although thermodynamic stability and solubility were not significantly altered. Moreover, in their publication, they expressively state they did not observe any solubility improvement of the native protein state of the engineered scFvs as determined by the PEG precipitation method. Other studies in which site directed mutagenesis was carried out on particular amino acid residues within the scFv also have been reported (see e.g., Tan, P. H. et al. (1988) *Biophys. J.* 75:1473-1482; Worn, A. and Pluckthun, A. (1998) *Biochem.* 37:13120-13127; Worn, A. and Pluckthun, A. (1999) *Biochem.* 38:8739-8750). In these various studies, the amino acid residues selected for mutagenesis were chosen based on their known positions within the scFv structure (e.g., from molecular modeling studies).

In another approach, the complementarity determining regions (CDRs) from a very poorly expressed scFv were grafted into the framework regions of an scFv that had been demonstrated to have favorable properties (Jung, S. and Pluckthun, A. (1997) *Prot. Eng.* 10:959-966). The resultant scFv showed improved soluble expression and thermodynamic stability.

Progress in the engineering of scFvs to improve solubility and other functional properties is reviewed in, for example, Worn, A. and Pluckthun, A. (2001) *J. Mol. Biol.* 305:989-1010. New approaches, however, are still needed that allow for rational design of immunobinders, in particular of scFvs with superior solubility. Moreover, methods of engineering scFvs, and other types of antibodies, to thereby impart improved solubility—especially solubility of the native protein—, are still needed.

SUMMARY OF THE INVENTION

This invention provides an immunobinder comprising a solubility enhancing motif in the variable heavy chain region $V_H$ as well as methods of engineering immunobinders, such as scFv antibodies, to confer improved solubility. In particular embodiments, the methods of the invention comprise the substitution of amino acids within a sequence of the variable heavy chain region and/or the variable light chain region of an immunobinder that are potentially problematic for solubility with preferred amino acid residues that confer improved solubility. For example, in certain preferred embodiments, a hydrophobic residue is substituted with a hydrophilic residue.

Preferably, the provided immunobinder, the immunobinder used in, or produced by, the engineering methods of the invention is an scFv, but other immunobinders, such as full-length immunoglobulins, Fab fragments, single domain antibodies (e.g., Dabs) and Nanobodies also can be engineered according to the method. The invention also encompasses immunobinders prepared according to the engineering method, as well as compositions comprising the immunobinders and a pharmaceutically acceptable carrier.

In one aspect, the invention provides an immunobinder comprising one of the following solubility enhancing motifs in the heavy chain amino acid positions 12, 103 and 144 (AHo numbering):

(a) Serine (S) at heavy chain amino acid position 12;
(b) Serine (S) at heavy chain amino acid position 103; and
(c) Threonine (T) at heavy chain amino acid position 144;
or
(a1) Serine (S) at heavy chain amino acid position 12;
(b1) Threonine (T) at heavy chain amino acid position 103; and
(c1) Serine (S) at heavy chain amino acid position 144; or
(a2) Serine (S) at heavy chain amino acid position 12;
(b2) Threonine (T) at heavy chain amino acid position 103; and
(c2) Threonine (T) at heavy chain amino acid position 144; or
(a3) Serine (S) at heavy chain amino acid position 12;
(b3) Serine (S) at heavy chain amino acid position 103; and
(c3) Serine (S) at heavy chain amino acid position 144.

In another aspect, the invention provides a method of engineering an immunobinder, the immunobinder comprising (i) a heavy chain variable region, or fragment thereof, the heavy chain variable region comprising $V_H$ framework residues and/or (ii) a light chain variable region, or fragment thereof, the light chain variable region comprising $V_L$ framework residues, the method comprising:

A) selecting at least two amino acid positions within the $V_H$ framework residues, the $V_L$ framework residues or the $V_H$ and $V_L$ framework residues for mutation; and B) mutating the at least two amino acid positions selected for mutation, wherein if the at least two amino acid positions selected for mutation are within the $V_H$ framework residues, the substitution is at one or more heavy chain amino acid positions selected from the group consisting 12, 103 and 144 (according to AHo numbering convention) and/or wherein if the one or more amino acid positions selected for mutation are within the $V_L$ framework residues, the substitution is at a light chain amino acid position selected from the group consisting of 15, 52 and 147 (according to AHo numbering convention; amino acid positions 15, 44 and 106 using Kabat numbering).

The at least two amino acid positions selected for mutation, and the amino acid residue(s) inserted at the selected position(s) are described in further detail below. The amino acid position numbering set forth below uses the AHo numbering system; the corresponding positions using the Kabat numbering system are described further herein and the conversion tables for the AHo and Kabat numbering systems are set forth below in the detailed description. The amino acid residues are set forth using standard one letter abbreviation code.

It has surprisingly been found that the presence of the indicated mutations at the indicated positions increase the overall solubility of the immunobinder without having a negative impact on other functional properties of the protein. For instance, in case of the combination of the three solubility enhancing mutations V12S, L144S and V103T in the $V_H$ of an scFv, it was found that said substitutions account for about 60% the entire scFv's solubility. This differs from attempts stated in the prior art to increase the expression yield of immunobinders. For example, U.S. Pat. No. 6,815,540 describes the modification of an immunobinder by decreasing the hydrophobicity in an intra-chain interdomain interface region. For said purpose, 16 positions in the variable heavy chain framework were identified which may be individually substituted by one or more amino acids selected from a group of 10 amino acids. It was found that the expression yield of the generated mutants was increased. Moreover, the same investigation group published in 1999, i.e. three years after the priority date of the mentioned US patent, a paper (see Jung, S., Honegger, A. and Pluckthun, A. (1997) *Prot. Eng.* 10:959-966) stating that the replacement of hydrophobic surface residues by more hydrophilic ones has been reported in several studies to improve production yield. According to the authors, the increase in production yield is due to improved kinetic portioning between correct folding and aggregation of misfolded material, while the solubility of the native protein is not even affected, nor its thermodynamic stability in a significant manner. It is hence clear to the skilled person that the solubility parameter Plückthun et al refer to concerns only soluble expression and not the overall solubility of the native protein.

BRIEF DESCRIPTION OF FIGURES

The invention will be better understood and objects other than those set forth above will become apparent when consideration is given to the following detailed description thereof. Such description makes reference to the annex drawings, wherein.

DETAILED DESCRIPTION OF THE INVENTION

Figure 1:
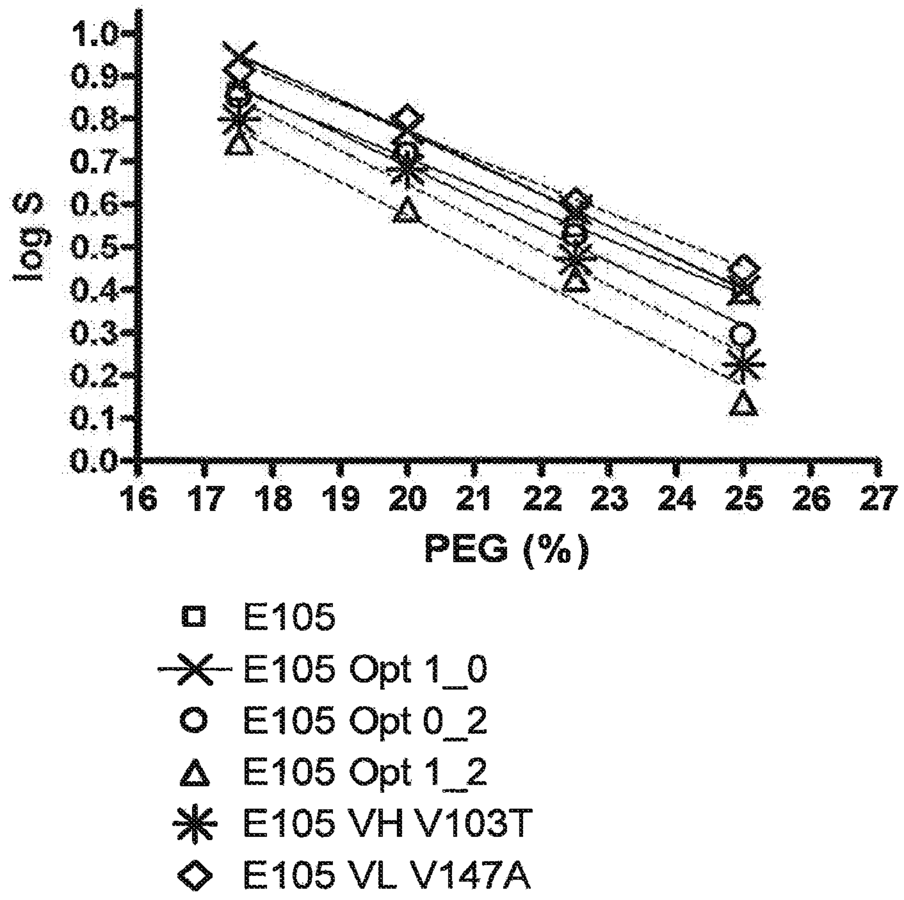
FIG. 1 depicts the PEG precipitation solubility curves of wild-type ESBA105 (E105) and solubility variants thereof.

The invention pertains to methods for enhancing the solubility of immunobinders. More specifically, the present invention discloses methods for optimizing immunobinders by introducing amino acid substitutions within the immunobinder that improve the solubility of the immunobinder. The invention also pertains to engineered immunobinders, e.g., scFvs, produced according to the methods of the invention.

So that the invention may be more readily understood, certain terms are first defined. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

The term "antibody" as used herein is a synonym for "immunoglobulin". Antibodies according to the present invention may be whole immunoglobulins or fragments thereof, comprising at least one variable domain of an immunoglobulin, such as single variable domains, Fv (Skerra A. and Pluckthun, A. (1988) *Science* 240:1038-41), scFv (Bird, R. E. et al. (1988) *Science* 242:423-26; Huston, J. S. et al. (1988) *Proc. Natl. Acad. Sci. USA* 85:5879-83), Fab, (Fab')2 or other fragments well known to a person skilled in the art.

The term "antibody framework" or "framework" as used herein refers to the part of the variable domain, either $V_L$ or $V_H$, which serves as a scaffold for the antigen binding loops of this variable domain (Kabat, E. A. et al., (1991) Sequences of proteins of immunological interest. NIH Publication 91-3242).

The term "antibody CDR" or "CDR" as used herein refers to the complementarity determining regions of the antibody which consist of the antigen binding loops as defined by Kabat E. A. et al., (1991) Sequences of proteins of immunological interest. NIH Publication 91-3242). Each of the two variable domains of an antibody Fv fragment contain, for example, three CDRs.

The term "single chain antibody" or "scFv" refers to a molecule comprising an antibody heavy chain variable region ($V_H$) and an antibody light chain variable region ($V_L$)

connected by a linker. Such scFv molecules can have the general structures: NH2-$V_L$-linker-$V_H$-COOH or NH2-$V_H$-linker-$V_L$-COOH.

As used herein, "identity" refers to the sequence matching between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are identical at that position. The "percentage identity" between two sequences is a function of the number of matching positions shared by the two sequences divided by the number of positions compared× 100. For instance, if 6 of 10 of the positions in two sequences are matched, then the two sequences have 60% identity. By way of example, the DNA sequences CTGACT and CAGGTT share 50% identity (3 of the 6 total positions are matched). Generally, a comparison is made when two sequences are aligned to give maximum identity. Such alignment can be provided using, for instance, the method of Needleman et al. (1970) *J. Mol. Biol.* 48: 443-453, implemented conveniently by computer programs such as the Align program (DNAstar, Inc.).

"Similar" sequences are those which, when aligned, share identical and similar amino acid residues, where similar residues are conservative substitutions for corresponding amino acid residues in an aligned reference sequence. In this regard, a "conservative substitution" of a residue in a reference sequence is a substitution by a residue that is physically or functionally similar to the corresponding reference residue, e.g., that has a similar size, shape, electric charge, chemical properties, including the ability to form covalent or hydrogen bonds, or the like. Thus, a "conservative substitution modified" sequence is one that differs from a reference sequence or a wild-type sequence in that one or more conservative substitutions are present. The "percentage similarity" between two sequences is a function of the number of positions that contain matching residues or conservative substitutions shared by the two sequences divided by the number of positions compared and multiplied by a factor 100. For instance, if 6 of 10 of the positions in two sequences are matched and 2 of 10 positions contain conservative substitutions, then the two sequences have 80% positive similarity.

"Amino acid consensus sequence" as used herein refers to an amino acid sequence that can be generated using a matrix of at least two, and preferably more, aligned amino acid sequences, and allowing for gaps in the alignment, such that it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids.

The amino acid sequence of a protein can be analyzed at various levels. For example, conservation or variability can be exhibited at the single residue level, multiple residue level, multiple residue level with gaps etc. Residues can exhibit conservation of the identical residue or can be conserved at the class level. Examples of amino acid classes include the class of amino acids with polar but uncharged side chains or R groups (Serine, Threonine, Asparagine and Glutamine); with positively charged R groups (Lysine, Arginine, and Histidine); with negatively charged R groups (Glutamic acid and Aspartic acid); with hydrophobic R groups (Alanine, Isoleucine, Leucine, Methionine, Phenylalanine, Tryptophan, Valine and Tyrosine); and the class of special amino acids (Cysteine, Glycine and Proline). Other classes are known to one of skill in the art and may be defined using structural determinations or other data to assess substitutability. In that sense, a substitutable amino acid can refer to any amino acid which can be substituted and maintain functional conservation at that position.

It will be recognized, however, that amino acids of the same class may vary in degree by their biophysical properties. For example, it will be recognized that certain hydrophobic R groups (e.g., Alanine, Serine, or Threonine) are more hydrophilic (i.e., of higher hydrophilicity or lower hydrophobicity) than other hydrophobic R groups (e.g., Valine or Leucine). Relative hydrophilicity or hydrophobicity can be determined using art-recognized methods (see, e.g., Rose et al., *Science,* 229: 834-838 (1985) and Cornette et al., *J. Mol. Biol.,* 195: 659-685 (1987)).

As used herein, when one amino acid sequence (e.g., a first $V_H$ or $V_L$ sequence) is aligned with one or more additional amino acid sequences (e.g., one or more $V_H$ or $V_L$ sequences in a database), an amino acid position in one sequence (e.g., the first $V_H$ or $V_L$ sequence) can be compared to a "corresponding position" in the one or more additional amino acid sequences. As used herein, the "corresponding position" represents the equivalent position in the sequence(s) being compared when the sequences are optimally aligned, i.e., when the sequences are aligned to achieve the highest percent identity or percent similarity.

As used herein, the term "antibody database" refers to a collection of two or more antibody amino acid sequences (a "multiplicity" of sequences), and typically refers to a collection of tens, hundreds or even thousands of antibody amino acid sequences. An antibody database can store amino acid sequences of, for example, a collection of antibody $V_H$ regions, antibody $V_L$ regions or both, or can store a collection of scFv sequences comprised of $V_H$ and $V_L$ regions. Preferably, the database is stored in a searchable, fixed medium, such as on a computer within a searchable computer program. In one embodiment, the antibody database is a database comprising or consisting of germline antibody sequences. In another embodiment, the antibody database is a database comprising or consisting of mature (i.e., expressed) antibody sequences (e.g., a Kabat database of mature antibody sequences, e.g., a KBD database). In yet another embodiment, the antibody database comprises or consists of functionally selected sequences (e.g., sequences selected from a QC assay).

The term "immunobinder" refers to a molecule that contains all or a part of the antigen binding site of an antibody, e.g., all or part of the heavy and/or light chain variable domain, such that the immunobinder specifically recognizes a target antigen. Non-limiting examples of immunobinders include full-length immunoglobulin molecules and scFvs, as well as antibody fragments, including but not limited to (i) a Fab fragment, a monovalent fragment consisting of the $V_L$, $V_H$, $C_L$ and $C_H1$ domains; (ii) a $F(ab')_2$ fragment, a bivalent fragment comprising two Fab fragments linked by a disulfide bridge at the hinge region; (iii) a Fab' fragment, which is essentially a Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment comprising the $V_L$ and $V_H$ domains of a single arm of an antibody, (vi) a single domain antibody such as a Dab fragment (Ward et al., (1989) *Nature* 341:544-546), which consists of a $V_H$ or $V_L$ domain, a Camelid (see Hamers-Casterman, et al.,

*Nature* 363:446-448 (1993), and Dumoulin, et al., *Protein Science* 11:500-515 (2002)) or a Shark antibody (e.g., shark Ig-NARs Nanobodies®; and (vii) a nanobody, a heavy chain variable region containing a single variable domain and two constant domains.

As used herein, the term "functional property" is a property of a polypeptide (e.g., an immunobinder) for which an improvement (e.g., relative to a conventional polypeptide) is desirable and/or advantageous to one of skill in the art, e.g., in order to improve the manufacturing properties or therapeutic efficacy of the polypeptide. In one embodiment, the functional property is stability (e.g., thermal stability). In another embodiment, the functional property is solubility (e.g., under cellular conditions). In yet another embodiment, the functional property is aggregation behaviour. In still another embodiment, the functional property is protein expression (e.g., in a prokaryotic cell). In yet another embodiment the functional property is the refolding efficiency following inclusion body solubilization in a corresponding purification process. In certain embodiments, antigen binding affinity is not a functional property desired for improvement. In still another embodiment, the improvement of the functional property does not involve a substantial change in antigen binding affinity.

The term "solubility" as used herein refers to the solubility of the native protein, i.e. of the monomeric, non-aggregated and functional immunobinder. "Enhanced solubility" means an improvement of the solubility of the native protein which is preferably determined by a least one of the following methods: PEG precipitation, ammonium sulphate precipitation, refolding yield or any other method to determine solubility that is known to the one skilled in the art. The PEG precipitation method is a method along the lines as described by Atha et al. in "Mechanism of Precipitation of Proteins by Polyethylene Glycols", *JBC,* 256: 12108-12117 (1981). The Ammonium sulphate precipitation can e.g. be carried out as follows: 10 μl aliquots of 20 mg/ml protein solutions are prepared to each of which 10 μl of $(NH4)_2SO_4$ solution of a different saturation grade (e.g. 35%, 33%, 31%, 29%, 25%, 20% and 15%) is added, followed by vortexing for 5 seconds and 30 minutes incubation at room temperature. After centrifugation at 6000 rpm at 4° C. for 30 minutes, the protein concentration in the supernatant is determined. In this method, the comparator for different proteins is the V50 value, which is the percentage of $(NH4)_2SO_4$ saturation at which 50% percent of the protein is precipitated. The V50 is determined from a plot of soluble protein determined in the supernatant against the applied percentage of $(NH4)_2SO_4$ saturation. The refolding yield corresponds to the percentage of correctly folded protein obtained from solubilized inclusion bodies in a corresponding manufacturing/purification process. The term solubility as used herein does not refer to soluble expression.

Immunobinders with Improved Solubility

In a first aspect, an immunobinder is provided comprising one of the following solubility enhancing motifs in the heavy chain amino acid positions 12, 103 and 144 (AHo numbering):

(a) Serine (S) at heavy chain amino acid position 12;

(b) Serine (S) at heavy chain amino acid position 103; and (c) Threonine (T) at heavy chain amino acid position 144; or (a1) Serine (S) at heavy chain amino acid position 12;

(b1) Threonine (T) at heavy chain amino acid position 103; and (c1) Serine (S) at heavy chain amino acid position 144; or (a2) Serine (S) at heavy chain amino acid position 12;

(b2) Threonine (T) at heavy chain amino acid position 103; and (c2) Threonine (T) at heavy chain amino acid position 144; or (a3) Serine (S) at heavy chain amino acid position 12;

(b3) Serine (S) at heavy chain amino acid position 103; and (c3) Serine (S) at heavy chain amino acid position 144; or It has surprisingly been found that the presence of the indicated amino acids at the indicated positions increase the overall solubility of the entire immunobinder. For instance, in case of the combination of the three solubility enhancing mutations V12S, L144S and V103T in the VH of an scFv, it was found that said substitutions account for about 60% the entire scFv's solubility. Since hydrophobic patches are conserved in the variable domains of all immunobinders, one or more substitutions at the indicated positions can be used to improve the solubility of any immunobinder.

The immunobinder is preferably an scFv antibody, a full-length immunoglobulin, a Fab fragment, a Dab or a Nanobody.

In a preferred embodiment, the immunobinder further comprises one or more amino acids of the group consisting of (a) Aspartic acid (D) at light chain amino acid position 31, (b) Glutamic acid (E) at light chain amino acid position 83, (c) Arginine (R) at heavy chain amino acid position 43, (d) Leucine (L) at heavy chain amino acid position 67 and (e) Alanine (A) at heavy chain amino acid position 78. The presence of one or more of the indicated amino acids at the corresponding positions confers to the immunobinder enhanced stability.

The amino acids indicated herein may be present in the naturally occurring immunobinder or derivative thereof, or the immunobinder may be engineered to incorporate one or more of the above mentioned amino acids.

In a preferred embodiment, the immunobinder disclosed herein specifically binds to human TNFα or to human VEGF.

Engineering of Immunobinders with Improved Solubility

As described in detail in the Examples, a sequence-based approach described herein has been used successfully to identify particular amino acid residue substitutions that confer improved solubility. The Examples list exemplary and preferred amino acid substitutions at defined amino acid positions within the $V_H$ regions and optionally in the $V_L$ region of an immunobinder (e.g., an scFv). The exemplary substitutions include substitution of problematic amino acid residues (e.g., solvent-exposed, hydrophobic residues) at amino acid positions that are more hydrophilic and that occur with greater frequency in the database (e.g., a mature antibody (KDB) database). A particularly preferred substitution is the most frequently occurring residue that is more hydrophilic than the problematic residue. In other embodiments, the more hydrophilic amino acid is selected from the group consisting of alanine (A), serine (S), and threonine (T).

Accordingly, the invention provides engineering methods in which one or more specified amino acid substitutions are introduced into an immunobinder, such as an scFv antibody. Such substitutions can be carried out using standard molecular biology methods, such as site-directed mutagenesis, PCR-mediated mutagenesis and the like.

As set forth in the Examples, the following amino acid positions have been identified as problematic amino acids (i.e., so-called "hydrophobic patches") for modification in the indicated $V_H$ or $V_L$ sequences:

$V_H$: amino acid positions 2, 4, 5, 12, 103 and 144; and $V_L$: amino acid positions 15, 52 and 147.

The numbering used is the AHo numbering system; conversion tables to convert the AHo numbering to the Kabat system numbering are set forth as Tables 1 and 2.

It has surprisingly been found that substitutions in two or more of $V_H$ positions 12, 103, 144 (according to AHo numbering system) affect the overall solubility of the entire immunobinder. Since hydrophobic patches are conserved in the variable domains of all immunobinders, a least two substitutions at the indicated positions can be used to improve the solubility of any immunobinder.

In one embodiment, the invention provides a method of engineering an immunobinder, such as an scFv antibody, in which at least two amino acid substitutions are made at one or more amino acid positions identified supra to thereby produce variant (i.e., mutated) forms of the immunobinders.

Thus, in another aspect, the invention provides a method of engineering an immunobinder, the method comprising:

A) selecting at least two amino acid positions within the $V_H$ region, the $V_L$ region or the $V_H$ and $V_L$ regions for mutation; and B) mutating at least two amino acid positions selected for mutation, wherein if the at least two amino acid positions selected for mutation are within the $V_H$ region, the substitution is at least two heavy chain amino acid positions selected from the group consisting of 12, 103 and 144 (according to AHo numbering convention; amino acid positions 11, 89 and 108 using Kabat numbering), and/or wherein if the one or more amino acid positions selected for mutation are within the $V_L$ region, the substitution is at a light chain amino acid position selected from the group consisting of 15, 52 and 147 (according to AHo numbering convention; amino acid positions 15, 44 and 106 using Kabat numbering).

In certain embodiments, the amino acid position is occupied by a hydrophobic amino acid (e.g., Leucine (L) or Valine (V)). In one embodiment, the amino acid at heavy chain amino acid position 12 is Valine (V). In another embodiment, the amino acid at heavy chain amino acid position 103 is Valine (V). In another embodiment, the amino acid at heavy chain amino acid position 144 is Leucine (L). In another embodiment, the amino acid at light chain amino acid position 15 is Valine (V). In another embodiment, the amino acid at light chain amino acid position 52 is Phenylalanine (F). In another embodiment, the amino acid at light chain amino acid position 147 is Valine (V).

Preferably, the mutating is a substitution of the amino acid at the selected amino acid position with a more hydrophilic amino acid. In other embodiments, the more hydrophilic amino acid is selected from serine (S) or threonine (T).

In certain embodiments, the method comprises: a) selecting at least two amino acid positions within the immunobinder for mutation; and b) mutating the at least two amino acid positions selected for mutation, wherein the mutating comprises at least two substitutions selected from the group consisting of:

(i) Serine (S) at heavy chain amino acid position 12 using AHo numbering (position 11 using Kabat numbering);

(ii) Serine (S) or Threonine (T) at heavy chain amino acid position 103 using AHo numbering (position 89 using Kabat numbering); and (iii) Serine (S) or Threonine (T) at heavy chain amino acid position 144 using AHo numbering (position 108 using Kabat numbering).

In a much preferred embodiment, at least one of the heavy chain amino acid positions 12, 103 and 144 is Threonine (T).

In yet other embodiments, the mutating comprises substitution with Threonine (T) a light chain amino acid position 15 using AHo or Kabat numbering and/or substitution with Alanine (A) at light chain amino acid position 147 using AHo numbering (position 106 using Kabat numbering convention).

In other embodiments, the mutating results in at least a 2-fold increase in solubility (e.g., a 2-fold, a 2.5-fold, a 3-fold, a 3.5-fold, a 4-fold or greater increase in solubility).

In another embodiment, thermal stability, refolding, expression yield, aggregation and/or binding activity of the immunobinder is not adversely affected by the mutating.

In certain embodiments, the mutating further comprises one or more stabilizing mutations at an amino acid position (AHo numbering convention) selected from the group consisting of: (a) Aspartic acid (D) at light chain amino acid position 31; (b) Glutamic acid (E) at light chain amino acid position 83; (c) Arginine (R) at heavy chain amino acid position 43; (d) Leucine (L) at heavy chain amino acid position 67; and (e) Alanine (A) at heavy chain amino acid position 78. These mutations have proven to have a effect on the stability of the immunobinder.

In another aspect, the invention provides an immunobinder prepared according to the method of the invention.

In certain exemplary embodiments, an immunobinder engineered according to the method of the invention is an art-recognized immunobinder which binds a target antigen of therapeutic importance or an immunobinder comprising variable regions (VL and/or VH regions) or one or more CDRs (e.g., CDRL1, CDRL2, CDRL3, CDRH1, CDRH2, and/or CDRH3) derived from the immunobinder of therapeutic importance. For example, immunobinders currently approved by the FDA or other regulatory authorities can be engineered according to the methods of the invention. More specifically, these exemplary immunobinders include, but are not limited to, anti-CD3 antibodies such as muromonab (Orthoclone® OKT3; Johnson&Johnson, Brunswick, N.J.; see Arakawa et al. J. Biochem, (1996) 120:657-662; Kung and Goldstein et al., Science (1979), 206: 347-349), anti-CD11 antibodies such as efalizumab (Raptiva®, Genentech, South San Francisco, Calif.), anti-CD20 antibodies such as rituximab (Rituxan®/Mabthera®, Genentech, South San Francisco, Calif.), tositumomab (Bexxar®, GlaxoSmithKline, London) or ibritumomab (Zevalin®, Biogen Idec, Cambridge Mass.)(see U.S. Pat. Nos. 5,736,137; 6,455,043; and 6,682,734), anti-CD25 (IL2Ra) antibodies such as daclizumab (Zenapax®, Roche, Basel, Switzerland) or basiliximab (Simulect®, Novartis, Basel, Switzerland), anti-CD33 antibodies such as gemtuzumab (Mylotarg®, Wyeth, Madison, N.J.—see U.S. Pat. Nos. 5,714,350 and 6,350,861), anti-CD52 antibodies such as alemtuzumab (Campath®, Millennium Pharmacueticals, Cambridge, Mass.), anti-GpIIb/gIIa antibodies such as abciximab (ReoPro®, Centocor, Horsham, Pa.), anti-TNFα antibodies such as infliximab (Remicade®, Centocor, Horsham, Pa.) or adalimumab (Humira®, Abbott, Abbott Park, Ill.—see U.S. Pat. No. 6,258,562), anti-IgE antibodies such as omalizumab (Xolair®, Genentech, South San Francisco, Calif.), anti-RSV antibodies such as palivizumab (Synagis®, Medimmune, Gaithersburg, Md.—see U.S. Pat. No. 5,824,307), anti-EpCAM antibodies such as edrecolomab (Panorex®, Centocor), anti-EGFR antibodies such as cetuximab (Erbitux®, Imclone Systems, New York, N.Y.) or panitumumab (Vectibix®, Amgen, Thousand Oaks, Calif.), anti-HER2/neu antibodies such as trastuzumab (Herceptin®, Genentech), anti-α4 integrin antibodies such as natalizumab (Tysabri®, Biogenldec), anti-CS antibodies such as eculizumab (Soliris®, Alexion Pharmaceuticals, Chesire, Conn.) and anti-VEGF antibodies such as bevacizumab (Avastin®, Genentech—see U.S. Pat. No. 6,884,879) or ranibizumab (Lucentis®, Genentech).

In certain exemplary embodiments, an immunobinder engineered according to the method of the invention is an art-recognized immunobinder described supra. In a preferred embodiment, the immunobinder is an scFv antibody. In other embodiments, the immunobinder is, for example, a full-length immunoglobulin, Dab, Nanobody or a Fab fragment.

Notwithstanding the foregoing, in various embodiments, certain immunobinders are excluded from being used in the engineering methods of the invention and/or are excluded from being the immunobinder composition produced by the engineering methods. For example, in various embodiments, there is a proviso that the immunobinder is not any of the scFv antibodies, or variants thereof, as disclosed in PCT Publications WO 2006/131013 and WO 2008/006235, such as ESBA105 or variants thereof that are disclosed in PCT Publications WO 2006/131013 and WO 2008/006235, the contents of each of which is expressly incorporated herein by reference.

Preferably, the immunobinder disclosed herein, used for the method disclosed herein or generated by the method disclosed herein, respectively, is an scFv antibody, but other immunobinders, such as full-length immunoglobulins, Fab fragments or any other type of immunobinder described herein (e.g., Dabs or Nanobodies) are also encompassed. In a preferred embodiment, the immunobinder as disclosed herein, used for the method disclosed herein or generated by the method disclosed herein, respectively, specifically binds to human TNFα or to human VEGF.

The invention further encompasses compositions comprising the immunobinders disclosed herein and a pharmaceutically acceptable carrier.

ScFv Compositions and Formulations

Another aspect of the invention pertains to scFv composition prepared according to the methods of invention. Thus, the invention provides engineered scFv compositions in which one or more solubility-enhancing mutations have been introduced into the amino acid sequence, as compared to an original scFv of interest, wherein the mutation(s) has been introduced into the position of a hydrophobic amino acid residue. In one embodiment, the scFv has been engineered to contain one mutated amino acid position (e.g., one framework position). In other embodiments, the scFv has been engineered to contain two, three, four, five, six, seven, eight, nine, ten or more than ten mutated amino acid positions (e.g., framework positions).

In certain embodiments, the mutating further comprises one or more stabilizing mutations described in PCT Application No. PCT/CH2008/000285, entitled "Methods of Modifying Antibodies, and Modified Antibodies with Improved Functional Properties", filed on Jun. 25, 2008 or US Provisional Application No. Ser. No. 61/069,056, entitled "Methods of Modifying Antibodies, and Modified Antibodies with Improved Functional Properties", filed on Mar. 12, 2008, both of which are incorporated herein by reference. For example the immunobinder may further comprise a substitution at an amino acid position (AHo numbering convention) selected from the group consisting of: (a) Aspartic acid (D) at light chain amino acid position 31; (b) Glutamic acid (E) at light chain amino acid position 83; (c) Arginine (R) at heavy chain amino acid position 43; (d) Leucine (L) at heavy chain amino acid position 67; and (e) Alanine (A) at heavy chain amino acid position 78. One or more mutations at the indicated positions have an effect on the overall stability of the entire immunobinder. In other embodiments, the mutating further comprises the following stabilizing mutations (AHo numbering convention): (a) Aspartic acid (D) at light chain amino acid position 31; (b) Glutamic acid (E) at light chain amino acid position 83; (c) Arginine (R) at heavy chain amino acid position 43; (d) Leucine (L) at heavy chain amino acid position 67; and (e) Alanine (A) at heavy chain amino acid position 78.

Another aspect of the invention pertains to pharmaceutical formulations of the scFv compositions of the invention. Such formulations typically comprise the scFv composition and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for, for example, intravenous, intramuscular, subcutaneous, parenteral, spinal, epidermal (e.g., by injection or infusion), or topical (e.g., to the eye or skin) administration. Depending on the route of administration, the scFv may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Antibody Position Numbering Systems

Conversion tables are provided for two different numbering systems used to identify amino acid residue positions in antibody heavy and light chain variable regions. The Kabat numbering system is described further in Kabat et al. (Kabat, E. A., et al. (1991) Sequences of Proteins of Immunological Interest, Fifth Edition, U.S. Department of Health and Human Services, NIH Publication No. 91-3242). The AHo numbering system is described further in Honegger, A. and Pluckthun, A. (2001) *J. Mol. Biol.* 309:657-670).

Heavy Chain Variable Region Numbering

TABLE 1

Conversion table for the residue positions in the Heavy Chain Variable Domain

| Kabat | AHo | Kabat | AHo | Kabat | AHo |
|---|---|---|---|---|---|
| 1 | 1 | 44 | 51 | 87 | 101 |
| 2 | 2 | 45 | 52 | 88 | 102 |
| 3 | 3 | 46 | 53 | 89 | 103 |
| 4 | 4 | 47 | 54 | 90 | 104 |
| 5 | 5 | 48 | 55 | 91 | 105 |
| 6 | 6 | 49 | 56 | 92 | 106 |
| 7 | 7 | 50 | 57 | 93 | 107 |
| * | 8 | 51 | 58 | 94 | 108 |
| 8 | 9 | 52 | 59 | 95 | 109 |
| 9 | 10 | 52a | 60 | 96 | 110 |
| 10 | 11 | 52b | 61 | 97 | 111 |
| 11 | 12 | 52c | 62 | 98 | 112 |
| 12 | 13 | * | 63 | 99 | 113 |
| 13 | 14 | 53 | 64 | 100 | 114 |
| 14 | 15 | 54 | 65 | 100a | 115 |
| 15 | 16 | 55 | 66 | 100b | 116 |
| 16 | 17 | 56 | 67 | 100c | 117 |
| 17 | 18 | 57 | 68 | 100d | 118 |
| 18 | 19 | 58 | 69 | 100e | 119 |
| 19 | 20 | 59 | 70 | 100f | 120 |
| 20 | 21 | 60 | 71 | 100g | 121 |
| 21 | 22 | 61 | 72 | 100h | 122 |
| 22 | 23 | 62 | 73 | 100i | 123 |
| 23 | 24 | 63 | 74 | * | 124 |
| 24 | 25 | 64 | 75 | * | 125 |
| 25 | 26 | 65 | 76 | * | 126 |
| 26 | 27 | 66 | 77 | * | 127 |
| * | 28 | 67 | 78 | * | 128 |
| 27 | 29 | 68 | 79 | * | 129 |
| 28 | 30 | 69 | 80 | * | 130 |
| 29 | 31 | 70 | 81 | * | 131 |
| 30 | 32 | 71 | 82 | * | 132 |
| 31 | 33 | 72 | 83 | * | 133 |
| 32 | 34 | 73 | 84 | * | 134 |

TABLE 1-continued

| Conversion table for the residue positions in the Heavy Chain Variable Domain | | | | | |
|---|---|---|---|---|---|
| Kabat | AHo | Kabat | AHo | Kabat | AHo |
| 33 | 35 | 74 | 85 | * | 135 |
| 34 | 36 | 75 | 86 | * | 136 |
| 35 | 37 | 76 | 87 | 101 | 137 |
| 35a | 38 | 77 | 88 | 102 | 138 |
| 35b | 39 | 78 | 89 | 103 | 139 |
| * | 40 | 79 | 90 | 104 | 140 |
| * | 41 | 80 | 91 | 105 | 141 |
| * | 42 | 81 | 92 | 106 | 142 |
| 36 | 43 | 82 | 93 | 107 | 143 |
| 37 | 44 | 82a | 94 | 108 | 144 |
| 38 | 45 | 82b | 95 | 109 | 145 |
| 39 | 46 | 82b | 96 | 110 | 146 |
| 40 | 47 | 83 | 97 | 111 | 147 |
| 41 | 48 | 84 | 98 | 112 | 148 |
| 42 | 49 | 85 | 99 | 113 | 149 |
| 43 | 50 | 86 | 100 | | |

Column 1, Residue position in Kabat's numbering system. Column 2, Corresponding number in AHo's numbering system for the position indicated in column 1. Column 3, Residue position in Kabat's numbering system. Column 4, Corresponding number in AHo's numbering system for the position indicated in column 3. Column 5, Residue position in Kabat's numbering system. Column 6, Corresponding number in AHo's numbering system for the position indicated in column 5

Light Chain Variable Region Numbering

TABLE 2

| Conversion table for the residue positions in the Light Chain Variable Domain | | | | | |
|---|---|---|---|---|---|
| Kabat | AHo | Kabat | AHo | Kabat | AHo |
| 1 | 1 | 43 | 51 | 83 | 101 |
| 2 | 2 | 44 | 52 | 84 | 102 |
| 3 | 3 | 45 | 53 | 85 | 103 |
| 4 | 4 | 46 | 54 | 86 | 104 |
| 5 | 5 | 47 | 55 | 87 | 105 |
| 6 | 6 | 48 | 56 | 88 | 106 |
| 7 | 7 | 49 | 57 | 89 | 107 |
| 8 | 8 | 50 | 58 | 90 | 108 |
| 9 | 9 | * | 59 | 91 | 109 |
| 10 | 10 | * | 60 | 92 | 110 |
| 11 | 11 | * | 61 | 93 | 111 |
| 12 | 12 | * | 62 | 94 | 112 |
| 13 | 13 | * | 63 | 95 | 113 |
| 14 | 14 | * | 64 | 95a | 114 |
| 15 | 15 | * | 65 | 95b | 115 |
| 16 | 16 | * | 66 | 95c | 116 |
| 17 | 17 | 51 | 67 | 95d | 117 |
| 18 | 18 | 52 | 68 | 95e | 118 |
| 19 | 19 | 53 | 69 | 95f | 119 |
| 20 | 20 | 54 | 70 | * | 120 |
| 21 | 21 | 55 | 71 | * | 121 |
| 22 | 22 | 56 | 72 | * | 122 |
| 23 | 23 | 57 | 73 | * | 123 |
| 24 | 24 | 58 | 74 | * | 124 |
| 25 | 25 | 59 | 75 | * | 125 |
| 26 | 26 | 60 | 76 | * | 126 |
| 27 | 27 | 61 | 77 | * | 127 |
| * | 28 | 62 | 78 | * | 128 |
| 27a | 29 | 63 | 79 | * | 129 |
| 27b | 30 | 64 | 80 | * | 130 |
| 27c | 31 | 65 | 81 | * | 131 |
| 27d | 32 | 66 | 82 | * | 132 |
| 27e | 33 | 67 | 83 | * | 133 |
| 27f | 34 | 68 | 84 | * | 134 |
| * | 35 | * | 85 | * | 135 |
| 28 | 36 | * | 86 | * | 136 |
| 29 | 37 | 69 | 87 | 96 | 137 |
| 30 | 38 | 70 | 88 | 97 | 138 |
| 31 | 39 | 71 | 89 | 98 | 139 |
| 32 | 40 | 72 | 90 | 99 | 140 |
| 33 | 41 | 73 | 91 | 100 | 141 |
| 34 | 42 | 74 | 92 | 101 | 142 |
| 35 | 43 | 75 | 93 | 102 | 143 |

TABLE 2-continued

| Conversion table for the residue positions in the Light Chain Variable Domain | | | | | |
|---|---|---|---|---|---|
| Kabat | AHo | Kabat | AHo | Kabat | AHo |
| 36 | 44 | 76 | 94 | 103 | 144 |
| 37 | 45 | 77 | 95 | 104 | 145 |
| 38 | 46 | 78 | 96 | 105 | 146 |
| 39 | 47 | 79 | 97 | 106 | 147 |
| 40 | 48 | 80 | 98 | 107 | 148 |
| 41 | 49 | 81 | 99 | 108 | 149 |
| 42 | 50 | 82 | 100 | | |

Column 1, Residue position in Kabat's numbering system. Column 2, Corresponding number in AHo's numbering system for the position indicated in column 1. Column 3, Residue position in Kabat's numbering system. Column 4, Corresponding number in AHo's numbering system for the position indicated in column 3. Column 5, Residue position in Kabat's numbering system. Column 6, Corresponding number in AHo's numbering system for the position indicated in column 5

Other Embodiments

It is understood that the invention also includes any of the methodologies, references, and/or compositions set forth in Appendices (A-C) of U.S. Provisional Patent Application Ser. No. 60/905,365 (priority giving application of WO 08/110348) and Appendices (A-I) of U.S. Provisional Patent Application Ser. No. 60/937,112 (priority giving application of WO09/000098), including, but not limited to, identified databases, bioinformatics, in silico data manipulation and interpretation methods, functional assays, preferred sequences, preferred residue(s) positions/alterations, framework identification and selection, framework alterations, CDR alignment and integration, and preferred alterations/mutations.

Additional information regarding these methodologies and compositions can be found in U.S. Ser. Nos. 60/819,378; and 60/899,907, and PCT Publication WO 2008/006235, entitled "scFv Antibodies Which Pass Epithelial And/Or Endothelial Layers" filed in July, 2006 and Feb. 6, 2007 respectively; WO06131013A2 entitled "Stable And Soluble Antibodies Inhibiting TNFα" filed Jun. 6, 2006; EP1506236A2 entitled "Immunoglobulin Frameworks Which Demonstrate Enhanced Stability In The Intracellular Environment And Methods Of Identifying Same" filed May 21, 2003; EP1479694A2 entitled "Intrabodies ScFv with defined framework that is stable in a reducing environment" filed Dec. 18, 2000; EP1242457B1 entitled "Intrabodies With Defined Framework That Is Stable In A Reducing Environment And Applications Thereof" filed Dec. 18, 2000; WO03097697A2 entitled "Immunoglobulin Frameworks Which Demonstrate Enhanced Stability In The Intracellular Environment And Methods Of Identifying Same" filed May 21, 2003; and WO0148017A1 entitled "Intrabodies With Defined Framework That Is Stable In A Reducing Environment And Applications Thereof" filed Dec. 18, 2000; and Honegger et al., J. Mol. Biol. 309:657-670 (2001).

Further, it is understood that the invention also includes methodologies and compositions suitable for the discovery and/or improvement of other antibody formats, e.g., full length antibodies or fragments thereof, for example Fabs, Dabs, and the like. Accordingly, the principles and residues identified herein as suitable for selection or alteration to achieve desired biophysical and/or therapeutic proprieties that can be applied to a wide range of immunobinders. In one embodiment, therapeutically relevant antibodies, for example, FDA-approved antibodies, are improved by modifying one or more residue positions as disclosed herein.

The invention is not limited to the engineering of immunobinders, however. For example, one skilled in the art will recognize that the methods of the invention can be applied to the engineering of other, non-immunoglobulin, binding molecules, including, but not limited to, fibronectin binding molecules such as Adnectins (see WO 01/64942 and U.S. Pat. Nos. 6,673,901, 6,703,199, 7,078,490, and 7,119,171), Affibodies (see e.g., U.S. Pat. Nos. 6,740,734 and 6,602,977 and in WO 00/63243), Anticalins (also known as lipocalins) (see WO99/16873 and WO 05/019254), A domain proteins (see WO 02/088171 and WO 04/044011) and ankyrin repeat proteins such as Darpins or leucine-repeat proteins (see WO 02/20565 and WO 06/083275).

The present disclosure is further illustrated by the following examples, which should not be construed as further limiting. The contents of all figures and all references, patents, published and non-published patent applications cited throughout this application are expressly incorporated herein by reference in their entireties.

Example 1: Generation of scFvs with Improved Solubility

In this example, a structural modeling and sequence analysis based approach was used to identify mutations in scFv framework regions that result in improved solubility.

a) Structural Analysis

The 3D structure of the ESBA105 scFv was modeled using the automated protein structure homology-modeling server, accessible via the ExPASy web server. The structure was analyzed according to the relative surface accessible to the solvent (rSAS) and residues were classified as follows: (1) Exposed for residues showing a rSAS≥50%; and (2) partially exposed for residues with a 50%≤rSAS≥25%. Hydrophobic residues with an rSAS≥25% were considered as hydrophobic patches. To validate the solvent accessible area of each hydrophobic patch found, calculations were done from 27 PDB files with high homology to ESBA105 and a resolution higher than 2.7 Å. The average rSAS and standard deviation were calculated for the hydrophobic patches and examined in detail for each of them (see Table 3).

TABLE 3

Assessment of the hydrophobic patches.

| Residue | Domain | Surface exposed to the solvent % | STDE % | rSAS | Sequence Variability | VH/ Antigen Interface | VH/VL Interface | VH/CH Interface |
|---|---|---|---|---|---|---|---|---|
| 2 | VH | 23.06 | 19.26 | 10-25% | 10-25% | >0-20% | >0-20% | 0 |
| 4 | VH | 0.66 | 1.26 | 0-10% | 0-10% | 0 | | 0 |
| 5 | VH | 61.85 | 12.96 | 50-75% | 10-25% | 0 | >0-20% | 0 |
| 12 | VH | 70.27 | 9.17 | 50-75% | 10-25% | 0 | 0 | 60-80% |
| 103 | VH | 35.85 | 5.85 | 25-50% | 10-25% | 0 | >0-2% | >0-2% |
| 144 | VH | 62.17 | 7.82 | 50-75% | 10-25% | 0 | 0 | >0-2% |
| 15 | VL | 49.59 | 9.77 | 25-50% | 10-25% | 0 | 0 | 0 |
| 147 | VL | 31.19 | 23.32 | 25-50% | 10-25% | 0 | 0 | 60-80% |

Column 1, residue position in AHo's numbering system. Column 2, Domain for the position indicated in column 1. Column 3, Average solvent accessible area calculations from 27 PDB files. Column 4, Standard deviations of column 3. Columns 5 to 9, Structural role of the hydrophobic patches retrieved from AHo's.

Most of the hydrophobic patches identified in ESBA105 corresponded to the variable-constant domain (VH/CH) interface. This correlated with previous findings of solvent exposed hydrophobic residues in an scFv format (Nieba et al., 1997). Two of the hydrophobic patches (VH 2 and VH 5) also contributed to the VL-VH interaction and were therefore excluded from subsequent analysis.

b) Design of Solubility Mutations

A total of 122 VL and 137 VH sequences were retrieved from Annemarie Honegger's antibody web-page (www.bioc.uzh.ch/antibody). The sequences originally corresponded to 393 antibody structures in Fv or Fab format extracted from the Protein Data Bank (PDB) (www.rcsb.org/pdb/home/home.do). Sequences were used for the analysis regardless of species or subgroup in order to increase the probability of finding alternative amino acids with higher hydrophilicity than the native residue. Sequences having more than 95% identity to any other sequence within the database were excluded to reduce bias. The sequences were aligned and analyzed for residues frequency. Sequence analysis tools and algorithms were applied to identify and select hydrophilic mutations to disrupt the hydrophobic patches in ESBA105. The sequences were aligned following AHo's numbering system for immunoglobulin variable domain (Honegger and Pluckthun 2001). The analysis was constrained to the framework regions.

The residues frequency, f(r), for each position, i, in the customized database was calculated by the number of times that particular residue is observed within the data set divided by the total number of sequences. In a first step, the frequency of occurrence of the different amino-acids was calculated for each hydrophobic patch. The residue frequency for each hydrophobic patch identified in ESBA105 was analyzed from the customized database described above. Table 4 reports the residue frequency at the hydrophobic patches divided by the totality of the residues present in the database.

TABLE 4

Residue frequency of 259 sequences from mature antibodies in an scFv or Fab format for the hydrophobic patches identified in ESBA105.

| | relative frequency in VH | | | | relative frequency in VL | |
|---|---|---|---|---|---|---|
| Residue | VH 4 | VH 12 | VH 103 | VH 144 | VL 15 | VL 147 |
| A | 0.23046215 | 0 | 0 | 0 | 3.8647343 | 0.176821923 |
| C | 0 | 0 | 0 | 0 | 0 | 0 |
| D | 0 | 0 | 0 | 0 | 0 | 0 |
| E | 0 | 0 | 0 | 0 | 0 | 0 |
| F | 0.483091787 | 0 | 0.483091787 | 0 | 0 | 0 |
| G | 0 | 0 | 0 | 0 | 0 | 0 |
| H | 0 | 0 | 0 | 0 | 0 | 0 |
| I | 0 | 2.415458937 | 9.661835749 | 0 | 5.314009662 | 70.38834951 |
| K | 0 | 0 | 0 | 0 | 0 | 0 |
| L | 96.61835749 | 89.85507246 | 7.246376812 | 27.0531401 | 45.89371981 | 15.53398058 |
| M | 0 | 0 | 10.62801932 | 1.93236715 | 0 | 0.970873786 |
| N | 0 | 0 | 0 | 0 | 0 | 0 |
| P | 0.966183575 | 0 | 0 | 0.966183575 | 21.73913043 | 0.485436893 |
| Q | 0 | 0 | 0 | 0.483091787 | 0 | 0 |
| R | 0 | 0 | 7.246376812 | 0 | 0 | 0 |
| S | 0 | 0.966183575 | 0 | 18.84057971 | 0 | 0 |
| T | 0 | 0 | 15.4589372 | 50.72463768 | 0.966183575 | 0 |
| V | 1.93236715 | 6.763285024 | 49.27536232 | 0 | 22.22222222 | 12.62135922 |
| W | 0 | 0 | 0 | 0 | 0 | 0 |
| Y | 0 | 0 | 0 | 0 | 0 | 0 |

In the second step the frequency of hydrophilic residues at the hydrophobic patches was used to design the solubility mutations by selecting the most abundant hydrophilic residue at each hydrophobic patch. Table 5 reports the solubility mutants identified using this approach. The hydrophobicity of the parental and mutant residues were calculated as average hydrophobicity of values published in several papers and expressed in function of the level of exposure of the side chain to the solvent.

TABLE 5

Different solubility mutations introduced in ESBA105 to disrupt the hydrophobic patches

| Residue | Domain | Surface exposed to the solvent % | Parental residue | Hydo-phobicity of parental residue | Solubility mutation | Hydo-phobicity of mutations |
|---|---|---|---|---|---|---|
| 4 | VH | 0.66 | L | 85.2 | A | 42.7 |
| 12 | VH | 70.27 | V | 73.2 | S | 28 |
| 103 | VH | 35.85 | V | 73.2 | T | 32.8 |
| 144* | VH | 62.17 | V | 73.2 | S | 28 |
| 15 | VL | 49.59 | V | 73.2 | T | 32.8 |
| 147 | VL | 31.19 | L | 85.2 | A | 42.7 |

*The hydrophobic patch at position 144 was exchanged not by the most abundant hydrophilic residue in the database but for Ser since this was already contained in the CDR's donor of ESBA105.

Column 1, residue position in AHo's numbering system. Column 2, Domain for the position indicated in column 1. Column 3, Average solvent accessible area calculations from 27 PDB files. Column 4, parental residues in ESBA105. Column 5, Average hydrophobicities of column 4, retrieved from AHo's. Columns 6, Most abundant hydrophilic residue at the position indicated in column 1. Average hydrophobicity of column 6 retrieved from AHo's.

c) Testing of Solubility ESBA105 Variants

The solubility mutations were introduced alone or in multiple combinations and tested for refolding yield, expression, activity and stability and aggregation patterns. Table 6 shows the various combinations of solubility mutations introduced in each ESBA105 optimized variant based on potential contribution to solubility and the level of risk that the mutation would alter antigen binding.

TABLE 6

Design of solubility variants for ESBA105.

| Hydrophobic surface residue | Domain | Parental residue | Mutants** Opt 1_0 | Opt 0_2 | Opt 1_2 | Opt 2_4 |
|---|---|---|---|---|---|---|
| 15 | VL | V | X | | X | X |
| 147* | VL | V | | | | X |
| 4* | VH | L | | | | X |
| 12 | VH | V | | X | X | X |
| 103* | VH | V | | | | X |
| 144 | VH | L | | X | X | X |

*Tested separately in a second round

**The underscore separates the number of mutations contained in the light and the heavy chain respectively.

Column 1, residue position in AHo's numbering system. Column 2, Domain for the position indicated in column 1. Column 3, Parental residue in ESBA105 at the different hydrophobic patches. Column 4, Different variants containing solubility mutations at the positions indicated, d) Solubility Measurements

Maximal solubilities of ESBA105 and variants were determined by the PEG precipitation method as initially described by Atha et al. (JBC, 256: 12108-12117 (1981)). In this method, the protein concentration in the supernatants of centrifugated PEG-protein mixtures is measured and logarithmically plotted against the PEG concentration. Protein solution of 20 mg/ml was mixed 1:1 with PEG solutions ranging from 30 to 50% saturation. These conditions were chosen based on the solubility profile observed for the wild-type ESBA105 after empirical determination of linear dependence of Log S versus Peg concentration (% w/v). Solubility curves of several examples of variant ESBA105 that exhibited superior solubility are depicted in FIG. 1. A complete list of solubility values is also provided in Table 7.

TABLE 7

| Estimated maximal solubility and activity of the mutants in comparison with the parental ESBA105. | | | | | | |
|---|---|---|---|---|---|---|
| Molecule | E105 | E105 Opt1_0 | E105 Opt0_2 | E105 Opt1_2 | E 105 VH V103T | E105 VL V147A |
| INTERCERPT | 1,956 | 2,228 | 2,179 | 2,163 | 2,223 | 2,047 |
| Maximal solubility | 90.36 | 169.04 | 151.01 | 145.55 | 167.11 | 111.43 |
| Activity relative to ESBA105 | 1 | 1.4 | 1.5 | 1.5 | 1.2 | 2 |

e) Thermostability Measurements

Figure 2:
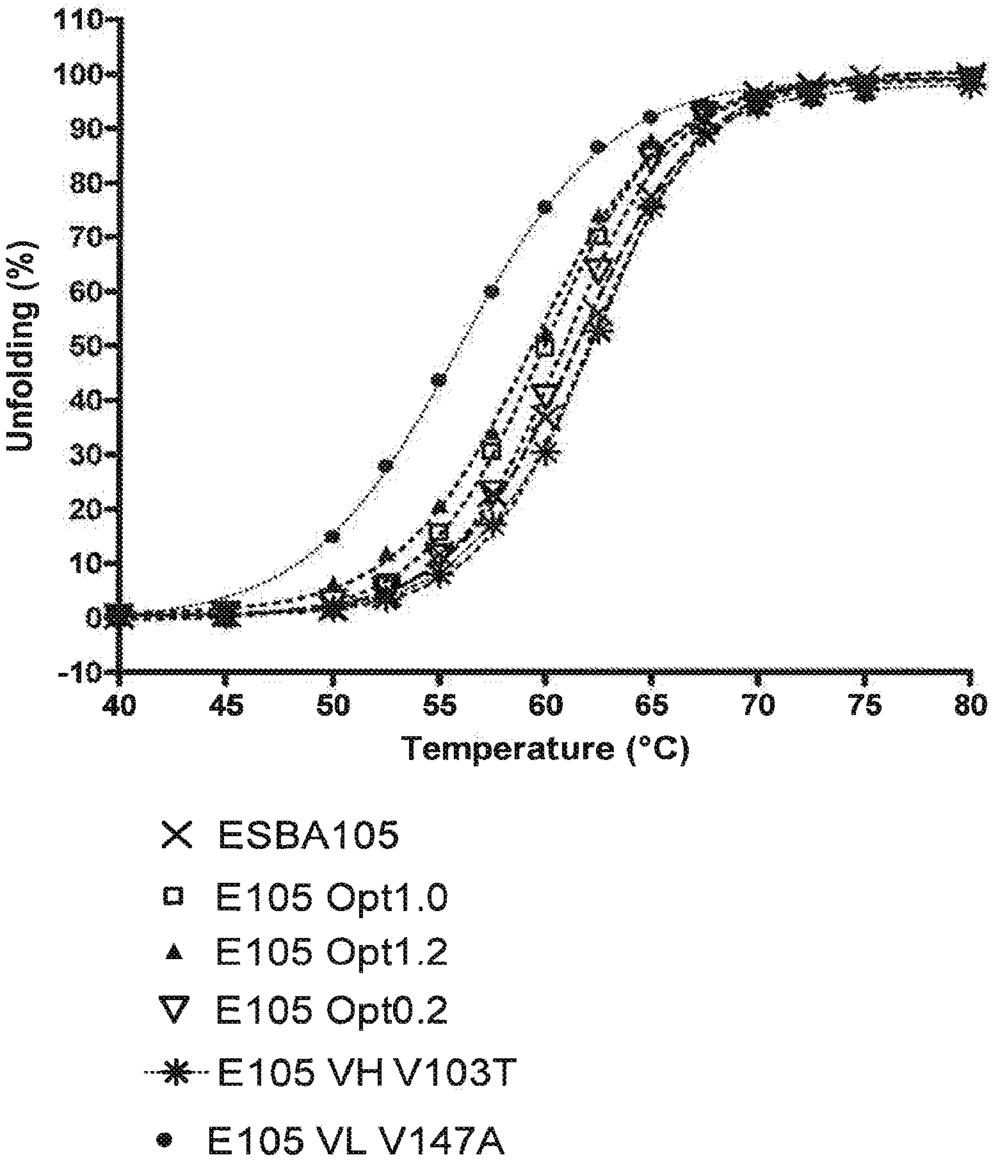
FIG. 2 depicts the thermal denaturation profiles for wild-type ESBA105 (E105) and solubility variants thereof as measured following thermochallenge at a broad range of temperatures (25-96° C.).

Thermostability measurements for the parental ESBA105 and the solubility follow ups were performed using FT-IR ATR spectroscopy. The molecules were thermochallenged to a broad range of temperatures (25 to 95° C.). The denaturation profile was obtained by applying a Fourier transformation to the interferogram signals (see FIG. 2). The denaturation profiles were used to approximate midpoints of the thermal unfolding transitions (TM) for every ESBA105 variant applying the Boltzmann sigmoidal model (Table 8).

TABLE 8

| Midpoints of the thermal unfolding transitions (TM) for every solubility variant. | | | | | | |
|---|---|---|---|---|---|---|
| | ESBA105 | E105 Opt1.0 | E105 Opt1.2 | E105 Opt0.2 | E105 VH V103T | E105 VL V147A |
| Boltzmann sigmoidal Best-fit values | | | | | | |
| BOTTOM | 0.3604 | −0.405 | 0.7032 | 0.4516 | 0.4691 | −0.6873 |
| TOP | 100.4 | 99.3 | 98.84 | 99.04 | 99.2 | 99.16 |
| V50 | 61.53 | 59.91 | 59.39 | 60.86 | 62.08 | 55.89 |
| SLOPE | 2.935 | 2.886 | 3.117 | 2.667 | 2.682 | 3.551 |
| Std. Error | | | | | | |
| BOTTOM | 0.5206 | 0.3471 | 0.6652 | 0.4953 | 0.3938 | 0.4754 |
| TOP | 0.5361 | 0.3266 | 0.6116 | 0.4891 | 0.4167 | 0.3714 |
| V50 | 0.1047 | 0.06658 | 0.1328 | 0.0949 | 0.07811 | 0.0919 |
| SLOPE | 0.09039 | 0.05744 | 0.1146 | 0.08199 | 0.06751 | 0.08235 |
| 95% Confidence Intervals | | | | | | |
| BOTTOM | −0.7432 to 1.464 | −1.141 to 0.3309 | −0.7071 to 2.114 | −0.5984 to 1.502 | −0.3658 to 1.304 | −1.695 to 0.3206 |
| TOP | 99.25 to 101.5 | 98.61 to 99.99 | 97.54 to 100.1 | 98.01 to 100.1 | 98.32 to 100.1 | 98.38 to 99.95 |
| V50 | 61.31 to 61.75 | 59.77 to 60.06 | 59.11 to 59.67 | 60.66 to 61.06 | 61.91 to 62.24 | 55.70 to 56.09 |
| SLOPE | 2.743 to 3.127 | 2.764 to 3.007 | 2.874 to 3.360 | 2.494 to 2.841 | 2.539 to 2.825 | 3.376 to 3.725 |
| Goodness of Fit | | | | | | |
| Degrees of Freedom | 16 | 16 | 16 | 16 | 16 | 16 |
| $R^2$ | 0.9993 | 0.9997 | 0.999 | 0.9994 | 0.9996 | 0.9996 |
| Absolute Sum of Squares | 26.18 | 10.8 | 37.2 | 24 | 16.14 | 15.11 |
| Sy.x | 1.279 | 0.8217 | 1.525 | 1.225 | 1.004 | 0.9719 |

iii. Aggregation Measurements

Figure 3:
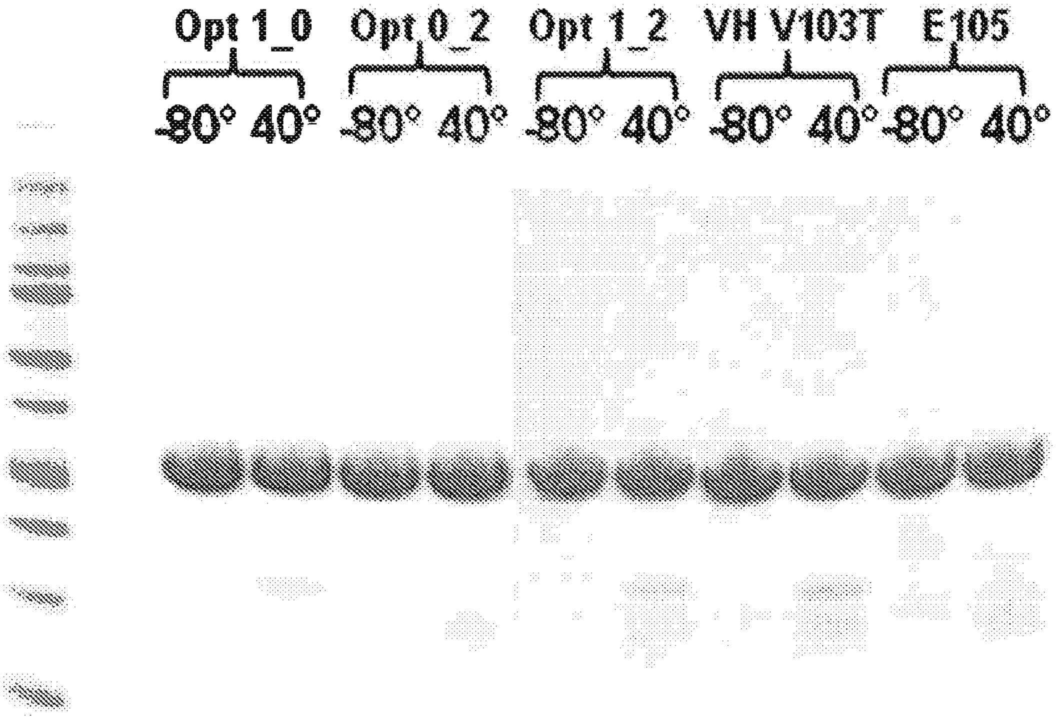
FIG. 3 depicts an SDS-PAGE gel which shows degradation behavior of various ESBA105 solubility mutants after two weeks of incubation under conditions of thermal stress.

ESBA105 and its solubility variants were also analyzed on a time-dependent test to assess degradation and aggregation behavior. For this purpose soluble proteins (20 mg/ml) were incubated at an elevated temperature (40° C.) in phosphate buffers at pH6.5. Control samples were kept at −80° C. The samples were analyzed after an incubation period of two weeks for degradation (SDS-PAGE) and aggregation (SEC). This allowed for the discarding of variants that were prone to degradation (see FIG. 3) or which exhibited a tendency to form soluble or insoluble aggregates (see Table 9).

TABLE 9

| Insoluble aggregation measurements. | |
|---|---|
| Protein | Protein loss (Insoluble aggregates) |
| ESBA105 | 0-10% |
| ESBA105 Opt 1_0 | 0-10% |
| ESBA105 Opt 0_2 | 0-10% |
| ESBA105 Opt 1_2 | 45-50% |
| ESBA105 VH V103T | 0-10% |

iv. Expression and Refolding of Solubility Variants

The solubility mutants were also tested for expression and refolding yield relative to the parent ESBA105 molecule. The results of these studies are shown in Table 10.

TABLE 10

Expression and refolding of solubility variants.

| | Hydrophobic surface residue | | | | | | | Expression relative. to | Refolding |
|---|---|---|---|---|---|---|---|---|---|
| | VH | | | | VL | | | ESBA105 | Yield mg/L |
| ESBA105 | L4 | V12 | V103 | L144 | V15 | F52 | V147 | 1.0 | 34 |
| Opt 1_0 | | | | | T | | | 1.15 | 12.5 |
| Opt 0_2 | | S | | S | | | | 1.10 | 35 |
| Opt 1_2 | | S | | S | T | | | 0.96 | 44 |
| Opt 2_4 | A | S | T | S | T | | A | 1.20 | not producible |
| VH L4A | | | | | | | | 1.0 | not producible |
| VH V103T | | | T | | | | | 1.1 | 55 |
| VL V147A | | | | | | | A | 1.2 | 20 |

Although all the hydrophilic solubility mutants exhibited improved solubility in comparison to the parental ESBA105 molecule, only some of these molecules exhibited suitable for other biophysical properties. For example, many variants had a reduced thermostability and/or refolding yield relative to the parental ESBA105 molecule. In particular, hydrophilic replacement at position $V_L$147 severely diminished stability. Solubility mutations that did not significantly affect thermal stability were therefore combined and subjected to further thermal stress to confirm their properties.

Three mutants containing a combination of four different solubility mutations (Opt1.0, Opt0.2 and $V_H$:V103T) significantly improved the solubility of ESBA105 without affecting reproducibility, activity or thermal stability. However, a mutant having the combined mutations of Opt1.0 and Opt0.2 in ESBA105 (Opt 1_2) exhibited an increased amount of insoluble aggregates after incubation for 2 weeks at 40° C. (see Table 9). This might be explained by the role of the Val at position $V_L$ 15 in a beta sheet turn, since Val has the greatest beta sheet propensity of all amino acid. This result demonstrated that a single solubility mutation at position VL 15 is tolerated, but not in combination with solubility mutants that disrupt other hydrophobic patches. Therefore, the mutations contained in Opt0_2 and VH:V103T were selected as best performers to improve solubility properties of scFv molecules.

Example 2: Generation of scFvs Having Enhanced Solubility and Stability

ESBA105 variants identified by solubility design were further optimized by substitution with stabilizing mutations identified by Quality Control (QC) assay. A total of 4 constructs were created which contained between 1 and 3 of the solubility mutations identified in Example 1 above, in combination with all stabilizing mutations found in QC 7.1 and 15.2 (i.e., D31N and V83E in the VL domain and V78A, K43 and F67L in the VH domain). All optimized constructs yielded more soluble protein than a wild-type scFv (see Table 11). The best construct consistently exhibited a greater than 2-fold increase in solubility over wild-type. Neither the activity nor the stability of the scFv molecules was significantly impacted by the combination of stabilizing and solubility enhancing mutations.

TABLE 11

ScFvs with optimized solubility and stability

| Protein | VL/VH Mutations | FTIR Tm (° C.) | PEG solubility (mg/ml) | Activity relative to E105 | kD |
|---|---|---|---|---|---|
| QC7.1D-N-15.2 | VL: D31N; V83E VH: V78A; K43R; F67L | 69.0 | 90 | 1.7 | $9.06 \times 10^{-10}$ |
| QC7.1D-N-15.2 VH V103T | VL: D31N; V83E VH: V78A; K43R; F67L; V103T | 68.9 | 106 | 1.5 | $8.79 \times 10^{-10}$ |
| QC7.1D-N-15.2 Opt 0_2 | VL: D31N; V83E VH: V12S; V78A; K43R; F67L; L144S | 66.6 | 121 | 1.2 | $8.12 \times 10^{-10}$ |
| QC7.1D-N-15.2 VH V103T Opt 0_2 | VL: D31N; V83E VH: V12S; V78A; K43R; F67L; V103T; L144S | 67.3 | 186 | 1.5 | $1.34 \times 10^{-9}$ |

The solubility values for all 4 variants were used to deconvolute the contribution of each mutation to the solubility of the scFv. All mutations appeared to contribute to the solubility of the scFv in an additive manner even though several of these residues are relatively close to one another both in primary sequence and within the 3D structure. The analysis indicated that a combination of three solubility-enhancing mutations in the VH domain (V12S, L144S, V103T (or V103S)) account for ~60% of scFv solubility. Since hydrophobic patches are conserved in the variable domains of all immunobinders, this optimal combination of mutations can be used to improve the solubility of virtually any scFv or other immunobinder molecule.

Example 3: Solubility Optimized Variant of Epi43max, a Potent TNFα Binder

Figure 4:
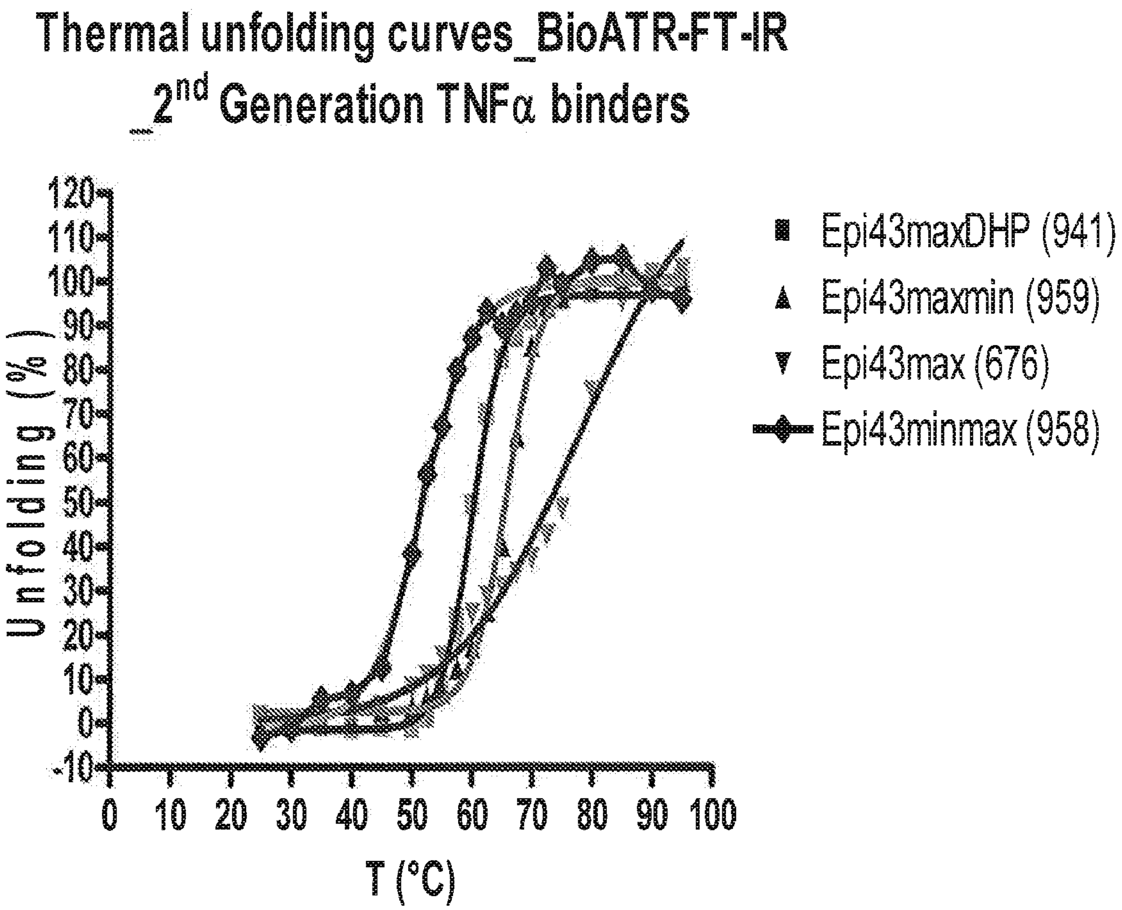
FIG. 4 depicts thermal denaturation curves of EP43max and its optimized variants as determined by FTIR analysis.

Table 12 depicts characterization data for three optimized variants of Epi43max, a potent TNF binder. EP43_maxDHP is a solubility enhanced variant of EP43max and comprises the three solubility enhancing mutations above (V→S at AHo position 12, V→T at AHo position 103, and L→T at AHo position 144). EP43_maxmin and EP43_minmax variants were generated by domain shuffling between "min" and "max" grafts. In particular, the "minmax" variant comprises the minimal graft (CDR-graft only) version of the light chain and maximal graft version of the heavy chain (i.e., grafted rabbit CDRs plus rabbit framework residues involved in antigen binding). Conversely, the "maxmin" variant comprised the maximal graft version of the light chain and the minimal graft version of the heavy chain. The thermal denaturation curves of EP43max and its optimized variants were compared by FTIR analysis (see FIG. 4). Epi43minmax was found to have a lower midpoint of unfolding that Epi43max. Moreover, the mimax variant exhibited a step unfolding transition, indicating the both domains unfold at very similar temperatures.

TABLE 12

Biophysical characterization data for three optimized variants of Epi43max, a potent TNF binder.

| | FW | L929* | Kon | Kaff | KD | FT-IR stability tm° C. | RF yield | Expression | Refolding screening | Purification |
|---|---|---|---|---|---|---|---|---|---|---|
| EP43_max | 1.4 | 6.4 | 2.28E+05 | 5.68E−05 | 2.49E−10 | 74.32 | 21.73 | +++ | Ok | Ok |
| EP43_maxDHP | 1.4 | 6.7 | 2.35E+05 | 2.73E−05 | 1.16E−10 | 60.15 | 17 | +++ | Ok | Ok |
| EP43_maxmin | 1.4 | Inactive | 1.46E+05 | 5.33E−03 | 3.66E−08 | 51.76 | 11 | +++ | Ok | Ok |
| EP43_minmax | 1.4 | 1.6 | 2.28E+05 | 1.98E−04 | 8.68E−10 | 65.81 | 46 | +++ | Ok | ok |

*L929 [EC50-E105/EC50-X], compared in mass units [ng/ml]

Example 4: Solubility Enhanced Derivatives of VEGF Immunobinders

In addition to the TNF immunobinders described above (ESBA105 and Epi43max), several solubility derivates of VEGF immunobinders were engineered according to the methods of the invention. In particular, these VEGF immunobinder variants were engineered to have a disrupted hydrophobic patch ("DHP") by selecting for the following residues: (a) Serine (S) at heavy chain amino acid position 12; (b) Serine (S) or Threonine (T) at heavy chain amino acid position 103; and (c) Serine (S) or Threonine (T) at heavy chain amino acid position 144. The biophysical characteristics of these DHP variants were compared to their wild-type counterparts. These characteristics included melting temperature or Tm (as determined by Bio-ATR), the percentage of β-sheet loss 60° C. (as determined by AquaSpec), the percentage of protein loss following precipitation at 60° C., solubility by ammonium sulfate precipitation, refolding yield in production and expression levels in *E. coli.*

Figure 5A:
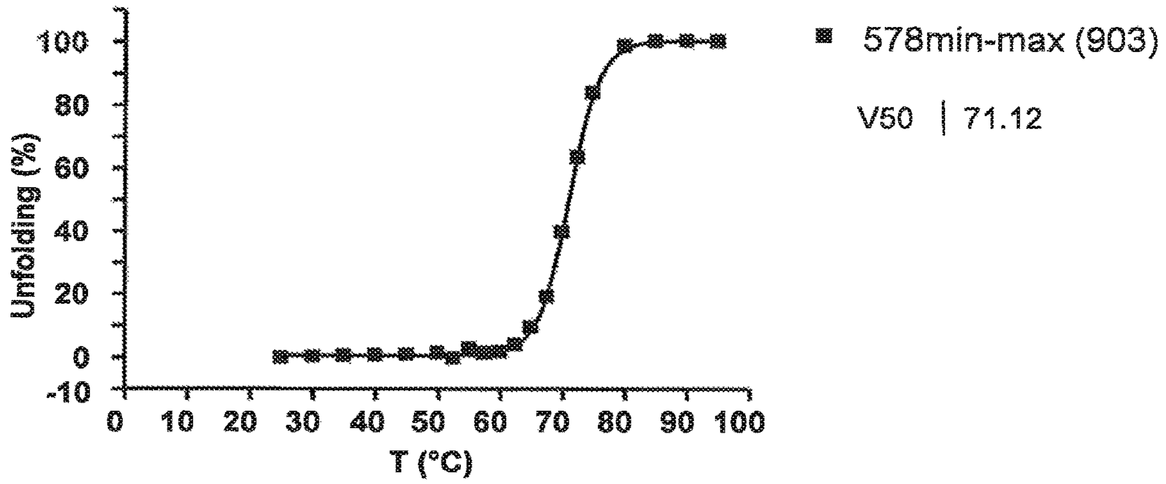
FIG. 5A and FIG. 5B depicts the thermal stability of 578 min-max and 578 min-max_DHP as measured by FT-IR.
Figure 5B:
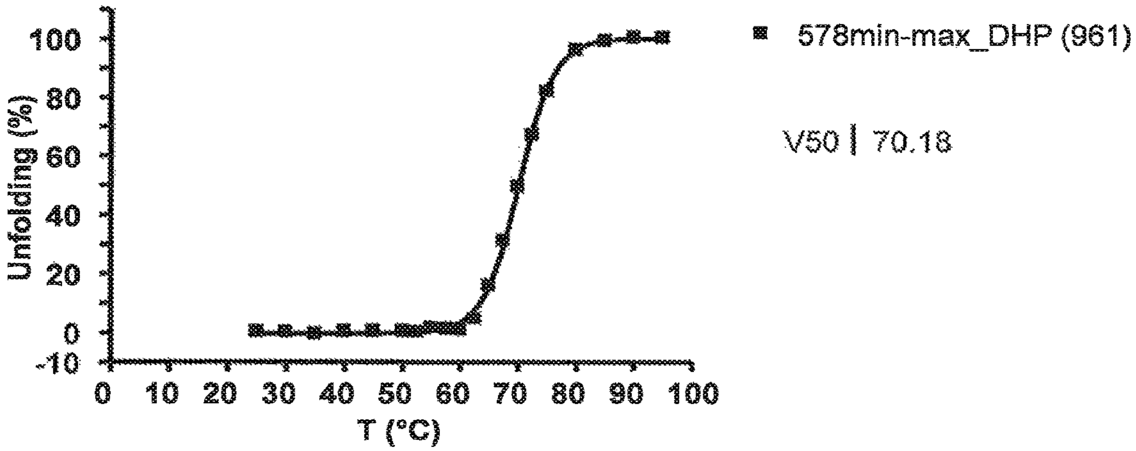
Figure 6A:
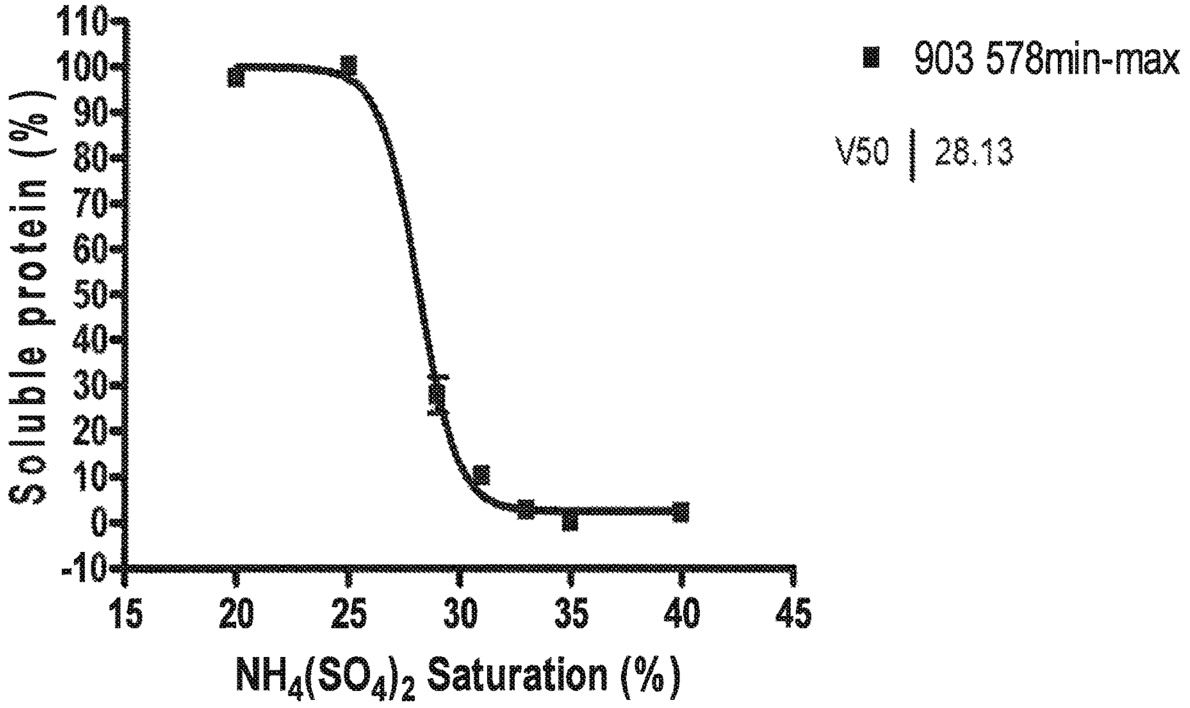
FIG. 6A and FIG. 6B illustrate solubility of 578 min-max and 578 min-max _DHP as determined by ammonium sulfate precipitation.
Figure 6B:
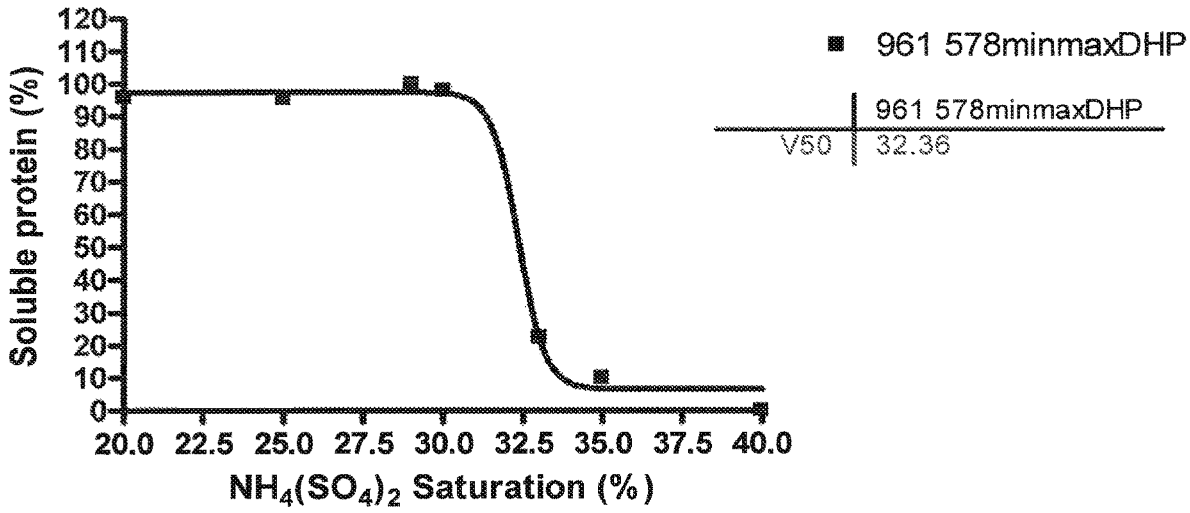

As depicted in Table 14 below, the solubility of one of the VEGF immunobinders (ESBA578minmax FW1.4 DHP) was significantly enhanced by introduction of the DHP motif. Moreover, other biophysical properties (e.g., thermal stability) were either not adversely affected or improved by introduction of the motif. The thermal stability curves used to determine melting temperature for 578 min-max and its solubility optimized variant (578 min-max_DHP) are depicted in FIG. 5 and Table 13, while the ammonium sulfate precipitation curves used to determine solubility values are depicted in FIG. 6.

TABLE 12

| | Epi43maxDHP (941) | Epi43maxmin (959) | Epi43max (676) | Epi43minmax (958) |
|---|---|---|---|---|
| V50 | 60.15 | 65.81 | 77.78 | 51.76 |
| SLOPE | 2.618 | 2.908 | 10.43 | 4.297 |
| $R^2$ | 0.9974 | 0.9969 | 0.9855 | 0.9936 |

TABLE 14

Biophysical Characterization of VEGF Immunobinders

| Immunobinder | TM [° C.] | % β Sheet Loss | % Protein Loss | Solubility [EC50 in % of $NH_4(SO_4)_2$ saturation] | Refolding Yield (mg/L) | Expression Level (arbitrary units) |
|---|---|---|---|---|---|---|
| 578-max | 70.36 | −1.93% | 16.20% | 27.24 | 12.5 | + |
| 578-max FW1.4_DHP | ND | ND | ND | ND | 11.6 | + |
| 578-min-max | 71.12 | −0.52% | 10.99% | 28.13 | 23.93 | +++ |
| 578-min-max FW1.4_DHP | 70.18 | −0.15% | 14.82% | 32.36 | 50.5 | +++ |

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An engineered immunobinder comprising rabbit complementarity determining regions (CDRs) and one of the following solubility enhancing motifs in the heavy chain amino acid positions 12, 103 and 144 (AHo numbering):

(a) Serine (S) at heavy chain amino acid position 12; Serine (S) at heavy chain amino acid position 103; and Threonine (T) at heavy chain amino acid position 144; or (b) Serine (S) at heavy chain amino acid position 12; Threonine (T) at heavy chain amino acid position 103; and Serine (S) at heavy chain amino acid position 144; or (c) Serine (S) at heavy chain amino acid position 12; Threonine (T) at heavy chain amino acid position 103; and Threonine (T) at heavy chain amino acid position 144.

2. The immunobinder of claim 1, further comprising:

(a) Aspartic acid (D) at light chain amino acid position 31;

(b) Glutamic acid (E) at light chain amino acid position 83;

(c) Arginine (R) at heavy chain amino acid position 43;

(d) Leucine (L) at heavy chain amino acid position 67; and/or (e) Alanine (A) at heavy chain amino acid position 78.

3. The immunobinder of claim 1, which is an scFv antibody, a full-length immunoglobulin, a Fab fragment, a Dab or a Nanobody.

4. A composition comprising the immunobinder of claim 1 and a pharmaceutically acceptable carrier.

* * * * *